(12) United States Patent
Giza et al.

(10) Patent No.: US 9,265,642 B2
(45) Date of Patent: Feb. 23, 2016

(54) BOOTLESS ANKLE BRACE

(75) Inventors: Eric Giza, Carmichael, CA (US);
Robert J. McCune, Escalon, CA (US);
Jeffrey L. Telles, Tracy, CA (US)

(73) Assignee: Top Shelf Manufacturing, LLC., Tracy, CA (US)

( * ) Notice: Subject to any disclaimer, the term of this patent is extended or adjusted under 35 U.S.C. 154(b) by 344 days.

(21) Appl. No.: 13/543,466

(22) Filed: Jul. 6, 2012

(65) Prior Publication Data

US 2013/0012855 A1 Jan. 10, 2013

Related U.S. Application Data

(60) Provisional application No. 61/504,960, filed on Jul. 6, 2011.

(51) Int. Cl.
*A61F 5/01* (2006.01)

(52) U.S. Cl.
CPC .................. *A61F 5/0111* (2013.01)

(58) Field of Classification Search
CPC .................................. A61F 5/0111
USPC .............. 602/27, 23, 5, 1, 65, 75, 28, 60, 61; 128/882; 36/89
See application file for complete search history.

(56) References Cited

U.S. PATENT DOCUMENTS

| | | | | |
|---|---|---|---|---|
| 3,506,000 | A * | 4/1970 | Baker | 602/65 |
| 5,067,486 | A * | 11/1991 | Hely | 602/27 |
| 5,288,286 | A * | 2/1994 | Davis | 602/6 |
| 7,497,839 | B2 * | 3/2009 | Quinn et al. | 602/27 |
| 7,908,771 | B2 * | 3/2011 | Foxen et al. | 36/89 |
| 8,454,545 | B1 * | 6/2013 | Weber et al. | 602/23 |
| 8,721,578 | B2 * | 5/2014 | Gaylord | 602/65 |
| 2006/0211968 | A1 * | 9/2006 | Gordon et al. | 602/27 |
| 2007/0149908 | A1 * | 6/2007 | Gordon, Jr. | 602/27 |
| 2009/0105704 | A1 * | 4/2009 | Gordon, Jr. | 606/27 |
| 2009/0112140 | A1 | 4/2009 | Gaylord et al. | |
| 2009/0192428 | A1 * | 7/2009 | DeBoer et al. | 602/27 |
| 2009/0247923 | A1 * | 10/2009 | Lundberg | 602/27 |
| 2013/0237894 | A1 * | 9/2013 | Lundberg | 602/27 |

OTHER PUBLICATIONS

ASO Vortex Ankle Stabilizer, 2012 Medical Specialties, Inc., www.medspec.com.

* cited by examiner

*Primary Examiner* — Victoria J Hicks
*Assistant Examiner* — Tarla Patel
(74) *Attorney, Agent, or Firm* — Christopher Pilling; Stephen A. Soffen

(57) ABSTRACT

A bootless ankle brace for treating an injured ankle. The brace includes a body panel, two stabilizing straps, and a binding strap. The user's foot is inserted into the body panel so that the body panel is located just above the ankle. The outside (lateral) stabilizing strap is brought forward across top of the foot and under the heel and secured to the opposite side of the ankle. This process is repeated with the inside (medial) stabilizing strap. Once both straps are secured, they are both tensioned (using finger loops) and re-secured to the side of the body panel. The ankle brace is secured by wrapping and securing an elastic cuff around the body panel.

10 Claims, 4 Drawing Sheets

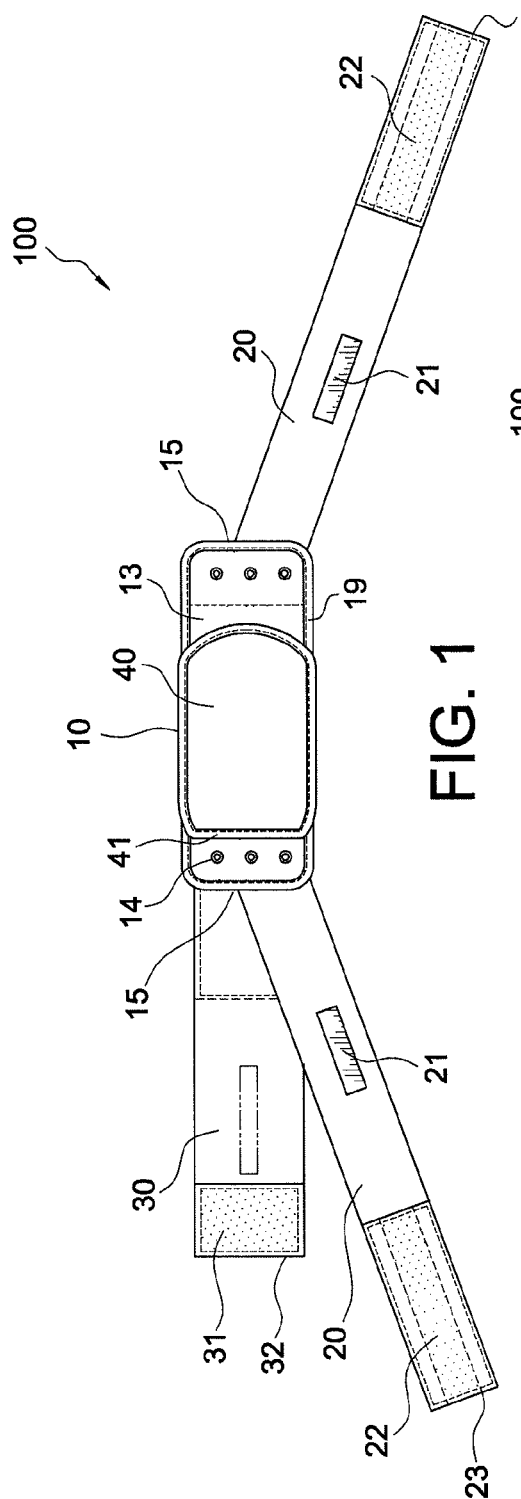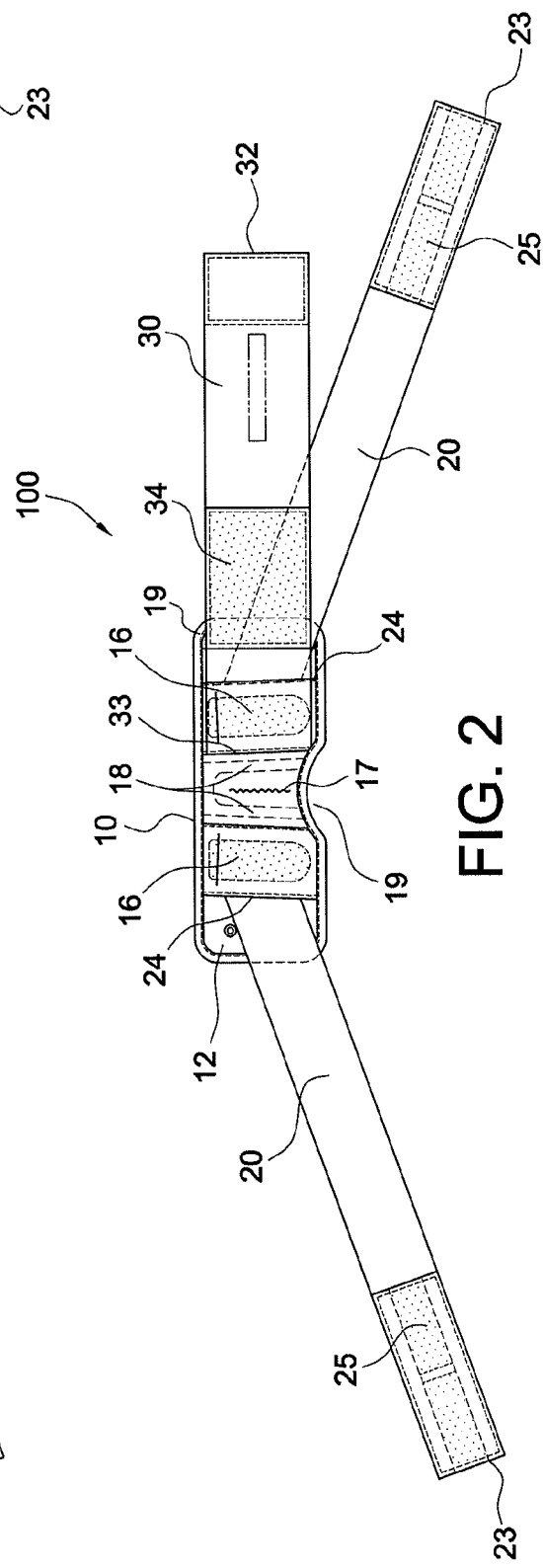

BOOTLESS ANKLE BRACE

This application claims the benefit of U.S. Provisional Application No. 61/504,960, filed Jul. 6, 2011, the disclosure of which is herein incorporated by reference.

FIELD OF THE INVENTION

The present invention is directed to an ankle brace with an improved and simplified design that eliminates the "boot-like" body member of conventional braces.

DESCRIPTION OF THE RELATED ART

Ankle braces are typically removably disposed over the foot and ankle of a user and include a "boot-like" body member or main body portion that extends under the user's foot. While such conventional designs provide support to the ankle joint, there is a need for an improved ankle brace with a simpler design that eliminates the full "boot" and provides a more intimate fit, allowing additional inversion and eversion control for the user. There is also need for an ankle brace that is less restrictive on the range of motion of the foot, less likely to migrate down the ankle, less likely to irritate the calcaneal tendon or Achilles' tendon and that does not require the user to wear and upsized shoe to accommodate the brace.

SUMMARY OF THE INVENTION

The present invention fulfills the above-noted need by providing a bootless ankle brace comprising a body panel, a first stabilizing strap with a first attachment end affixed to the body panel and a first free end with a releasable closure device, a second stabilizing strap with a second attachment end affixed to the body panel and a second free end with a releasable closure device, and a binding strap with a binding strap attachment end affixed the body panel. The body panel includes an inner lining and an outer panel attached to the inner lining at a vertical seam. A pliable buttress is provided between the outer panel and inner lining at the vertical seam. The pliable buttress is formed of a padding material such as foam or rubber. The body panel is provided with a plurality of eyelets to accommodate one or more laces for drawing the ends of the body panel together and wrapping the body panel around a leg at or near the ankle. Straps or other closure devices can be used instead of laces. The first and second stabilizing straps are provided in a belt-like configuration, and have releasable closure devices on their free ends. Similarly, the binding strap has a releasable closure device on its free end.

The bootless ankle brace is used to treat an ankle by inserting the foot inside the body panel and positioning the body panel just above the ankle, wrapping the first stabilizing strap over the top of a foot and under an instep in the foot, and securing the first stabilizing strap to the body panel, and then repeating this step with the second stabilizing strap. After tightening the stabilizing straps, the brace is then secured by wrapping the binding strap around the body panel, and securing the binding strap to the body panel. A heel notch may be provided in the body panel, in which case the heel of the foot can be aligned with the heel notch.

BRIEF DESCRIPTION OF THE DRAWINGS

Other features and advantages of the present invention will become apparent when the following detailed description is read in conjunction with the accompanying drawings, in which:

FIG. 1 is a top view of the inside of an ankle brace of the present invention with the tongue illustrated over the inner lining and the lacing not illustrated.

FIG. 2 is a top view of the outside of the ankle brace of FIG. 1 with both the tongue and lacing not illustrated.

DETAILED DESCRIPTION OF THE PREFERRED EMBODIMENT

Figure 3:
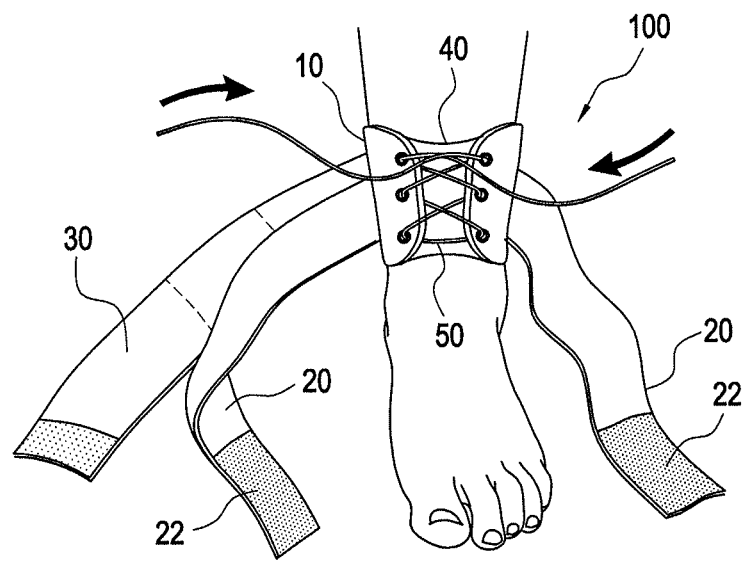
FIG. 3-7 are perspective views illustrating the steps involved in applying the ankle brace onto an ankle.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide an ankle orthosis with an improved and simplified design to apply compression forces without the "boot-like" body member.

FIGS. 1 through 7 illustrate an exemplary embodiment of ankle brace or orthosis 100 which provides localized compressive forces about the ankle without requiring a full "boot-like" main body member that extends under a user's foot. The present invention includes a simple "bootless" design, including a body panel 10 that is secured to the ankle with a lacing arrangement 50 and stabilizing straps 20 that are wrapped around the foot, and then stabilized in the desired configuration with a binding strap 30.

As shown in FIGS. 1 and 2, the body panel 10 includes an outer panel 12 and an inner lining 13 which are joined by an overedge binding strip 19 that is sewn along the perimeter of the body panel 10. The front edges of the body panel 10 are flexible so that, when in place, the body panel 10 conforms to the anterior surface of the ankle. The outer panel 12 may comprise nylon, neoprene, or other flexible fabric material, for example, to anatomically fit around the ankle. The inner lining 13 may comprise wool, cotton, or synthetic material, for example, to absorb fluid, prevent migration of the orthosis 100, and provide a more intimate fit around the ankle. The body panel 10 extends vertically along the length of the ankle and does not extend under the foot. Thus, a more economical orthosis is provided, requiring less material and eliminating the need for the user to upsize his or her shoe to accommodate the brace. Additionally, advantageously, in accordance with the present invention, the body panel 10 is not obstructed by a "boot-like" body member and thus provides localized hoop compression of the tibia and fibula to better maintain the ankle syndesmosis.

As shown in FIG. 1, a plurality of eyelets 14 are disposed along the length of the free end 15 of each side of the body panel 10. The eyelets 14 do not extend over the dorsal portion of foot because the "boot-like" portion of the brace has been eliminated in the present invention. Thus, the orthosis 100 of the present invention is less restrictive on the normal range of motion of the foot and ankle.

As shown in FIG. 3, a flexible strand of lacing 50 is threaded through the eyelets 14 to interconnect the free ends 15 of the body panel 10. This permits the free ends of the brace to be drawn toward each other in the conventional manner, and thereby causing the body panel 10 to be tightly secured directly around the ankle of the user. In lieu of laces, a single strap could be used to draw the sides of the brace together.

As shown in FIG. 2, the body panel 10 also includes a rear edge portion which extends vertically along the posterior of the ankle at a vertical seam 17 between the outer panel 12 and inner lining 13. This rear edge portion extends along the Achilles tendon of the user. A heel notch 19 is located at the bottom of the body panel 10 and is curved to prevent irritation to the Achilles tendon and reduce restriction of normal movement of the foot and ankle. A pliable buttress 18 is placed between the outer panel 12 and inner lining 13, surrounding the vertical seam 17. The pliable buttress 18 may comprise foam, rubber, or other padding material, for example, to anatomically fit around the ankle, prevent migration of the orthosis, and reduce insertional Achilles irritation.

As shown in FIG. 1, the orthosis 100 is preferably also provided with a tongue 40 secured to the body panel 10 at one end by an attachment seam 41. The tongue 40 may be formed of, for example, mesh, nylon, or other flexible fabric.

The orthosis 100 of the present invention is additionally provided with stabilizing straps 20, each having a belt-like configuration, as shown in FIGS. 1 and 2. Stabilizing strap 20 may be, for example, nylon, neoprene, or other flexible, non-elastic fabric material and comprise a free end 23 and an attachment end 24. Stabilizing strap 20 has two releasable securing means 22 and 25 located on either side of the free end 23 of the stabilizing strap 20, which may be a hook-and-loop strip (such as those manufactured under the VELCRO® brand name), hook, snap, or other releasable closure device.

Stabilizing strap 20 may optionally be provided with a non-slip strip 21 comprised of non-slip tape, grip tape, rubber, or other non-slip material located on one side of the stabilizing strap 20. The non-slip strip 21 secures the stabilizing strap 20 to the foot and prevents the stabilizing strap 20 from slipping out under the foot. The stabilizing straps 20 are secured around the foot and not around a "boot-like" body member, and thus provide increased inversion and eversion control of the foot.

As shown in FIGS. 1 and 2, the orthosis 100 may be provided with a binding strap 30 comprised of nylon, neoprene, or other flexible, elastic material. The binding strap 30 is secured to the body panel 10 at the attachment end 33. The binding strap 30 further secures the body panel 10 to the patient's ankle.

As illustrated in FIGS. 3-7, the orthosis 100 is adapted to be placed on either foot of the user and can be worn over top of a sock. As shown in FIG. 3, after loosening all straps and laces, the user places his/her foot inside the body portion 10 of the brace, making sure the brace is just above the ankle and the tongue 40 is between the skin and the lacing 50. The free ends of the body panel 15 are drawn together with the lacing 50.

Figure 4:
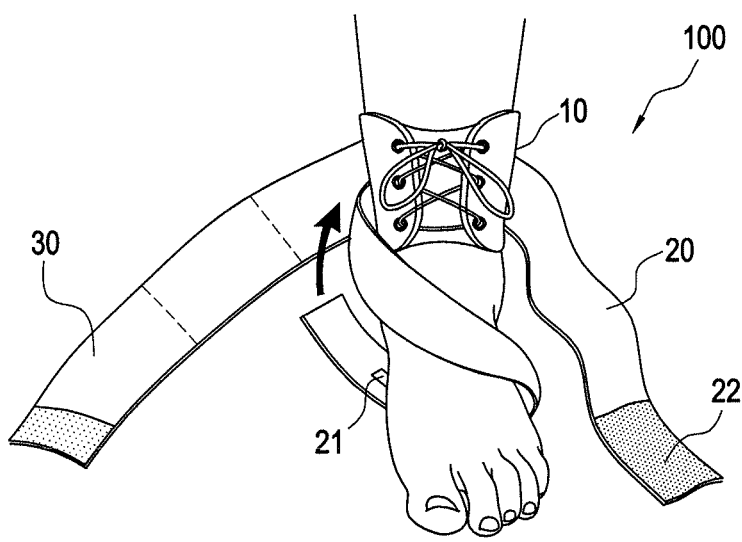
Figure 5:
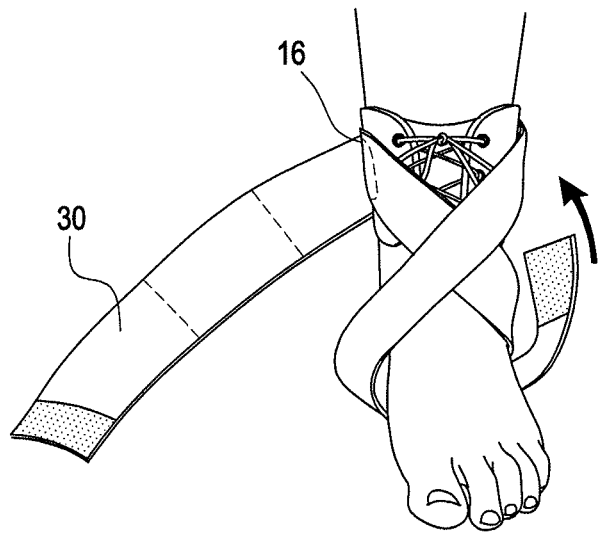

As shown in FIG. 4, with the ankle at a 90° angle, the outside (lateral) stabilizing strap 20 is brought forward across top of the foot and then underneath the heel, positioning the optional non-slip strip 21 under the instep of the foot. The stabilizing strap 20 is then secured to the opposite side of the ankle using releasable closure means 16 on the outside of body panel 10. This process is repeated with the inside (medial) stabilizing strap 20, as illustrated in FIG. 5, and the strap is secured to opposite side of the ankle as the first strap. With the user seated, both straps 20 are then tensioned, using finger loops (not shown) to pull up away firmly on both straps, and the tightened straps are then reapplied to the respective sides of the brace.

Figure 6:
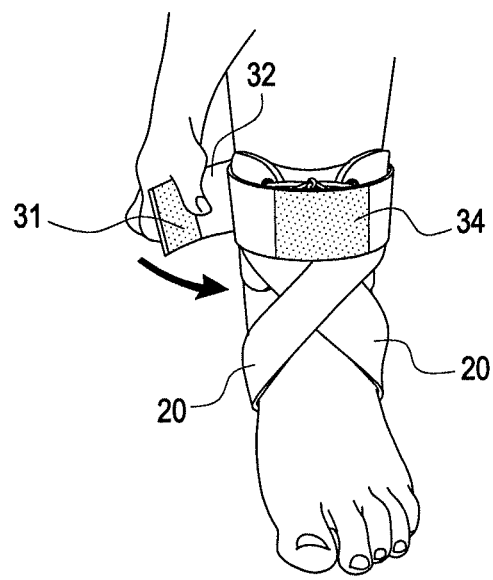
Figure 7:
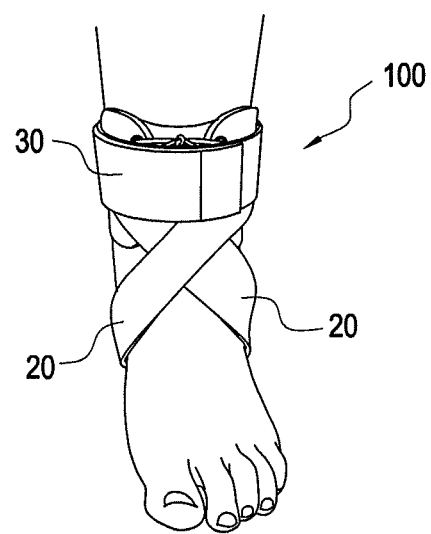

As shown in FIGS. 6 & 7, the orthosis 100 is secured by wrapping the binding strap 30 around the body panel 10 and attaching the releasable securing means 31 located on the free end 32 of the binding strap 30 to the releasable securing means 34 located on the body of the binding strap 30.

As described above, the ankle brace of the present invention advantageously provides a simplified "bootless" design which provides additional inversion and eversion control for the user, while also reducing restrictions on the normal range of motion of the foot and ankle. The bootless design of the present invention also advantageously provides more localized hoop compression on the ankle syndesmosis, less irritation of the calcaneal tendon or Achilles' tendon, and reduced migration of the brace down the ankle, while also eliminating the need for the user to wear upsized shoes to accommodate the brace.

The above description and drawings illustrate preferred embodiments which achieve the objects, features and advantages of the present invention. It is not intended that the present invention be limited to the illustrated embodiments.

We claim:

1. A method of treating an ankle, comprising steps:
   (a) inserting a foot of a user into a body panel having a bottom perimeter surface of a bootless ankle brace, such that the bottom perimeter surface is just above an ankle of the user and the body panel does not extend under the foot;
   (b) aligning an Achilles tendon with a heal notch in the bottom perimeter surface of the body panel, wherein the heal notch is curved and designed to prevent the ankle brace from overlapping and irritating the Achilles tendon while reducing restriction of normal movement of the foot and ankle;
   (c) wrapping a first stabilizing strap over a top surface of the foot;
   (d) wrapping the first stabilizing strap under an instep in the foot;
   (e) securing the first stabilizing strap to the body panel;
   (f) wrapping a second stabilizing strap over the top surface of the foot;
   (g) wrapping the second stabilizing strap under an instep in the foot;
   (h) securing the second stabilizing strap to the body panel;
   (i) wrapping a binding strap around the body panel; and
   (j) securing the binding strap to the body panel.

2. The method of claim 1, wherein the first stabilizing strap and second stabilizing straps are wrapped around opposite sides of the top of the foot.

3. The method of claim 1, further providing a step wherein the body panel is tightened around the leg with laces.

4. The method of claim 1, wherein the first and second stabilizing straps are secured to the body panel using a releasable closure device selected from the group consisting of at least one of a hook-and-loop strip, hook, snap, or a combination thereof.

5. The method of claim 1, wherein in step (j), the binding strap is secured to the body panel with a releasable closure device selected from the group consisting of at least one of a hook-and-loop strip, hook, snap, or a combination thereof.

6. The method of claim 1, wherein the first and second stabilizing straps each comprise a non-slip strip located on an interior surface of each stabilizing strap, wherein the non-slip strip is configured to prevent the stabilizing strap from slipping out from under the foot.

7. The method of claim 6, wherein the non-slip strip is selected from the group consisting of non-slip tape, grip tape, or rubber.

8. The method of claim 1, wherein step (c) is carried out prior to step (d).

9. The method of claim 1, wherein step (f) is carried out prior to step (g).

10. The method of claim 1, wherein the first and second stabilizing straps are comprised of a non-elastic material.

* * * * *